United States Patent [19]

Cavagna et al.

[11] Patent Number: 5,571,102
[45] Date of Patent: Nov. 5, 1996

[54] SYSTEM FOR SPINAL OSTEOSYNTHESIS

[76] Inventors: Remi Cavagna, 29 rue Sainte Anne, Ploemeur 56270; Robert Clerc, Carimel, Languenan 22130, both of France

[21] Appl. No.: 505,903

[22] Filed: Jul. 24, 1995

Related U.S. Application Data

[63] Continuation of Ser. No. 121,827, Sep. 14, 1993, abandoned.

[30] Foreign Application Priority Data

Sep. 15, 1992 [FR] France .................................. 92 10956

[51] Int. Cl.⁶ .................................................. A61B 17/70
[52] U.S. Cl. ............................................. 606/61; 606/73
[58] Field of Search .................... 606/61, 60, 73, 606/72; 623/17; 411/427

[56] References Cited

U.S. PATENT DOCUMENTS

| | | | |
|---|---|---|---|
| 1,529,549 | 3/1925 | Owen | 411/427 |
| 4,648,388 | 3/1987 | Steffee . | |
| 4,653,481 | 3/1987 | Howland et al. . | |
| 4,719,905 | 1/1988 | Steffee . | |
| 4,771,767 | 9/1988 | Steffee . | |
| 5,024,213 | 6/1991 | Asher et al. . | |
| 5,127,912 | 7/1992 | Ray et al. . | |
| 5,129,900 | 7/1992 | Asher et al. . | |
| 5,171,279 | 12/1992 | Mathews | 606/61 |
| 5,176,680 | 1/1993 | Vignaud et al. | 606/73 |

FOREIGN PATENT DOCUMENTS

| | | |
|---|---|---|
| 0348581 | 1/1990 | European Pat. Off. . |
| 0383992 | 8/1990 | European Pat. Off. . |
| 0443894 | 8/1991 | European Pat. Off. . |
| 2615095 | 11/1988 | France . |
| 3924050 | 1/1991 | Germany . |
| 2178323 | 2/1987 | United Kingdom . |

*Primary Examiner*—Guy Tucker
*Attorney, Agent, or Firm*—Birch, Stewart, Kolasch & Birch, LLP

[57] ABSTRACT

A system for spinal osteosynthesis is provided comprising a pedicle screw having a pedicle thread for introduction into the pedicle of a vertebra and a saddle thread adapted to receive a saddle member, a rod, at least one saddle member with a hole of a diameter substantially corresponding to the diameter of the saddle thread and a throat portion the axis of which is substantially perpendicular to the axis of the head and which includes a passage for the rod. A device secures the saddle member on the screw adapted to render the pedicle screw integral with the saddle member at the head thereof prior to application of mechanical effort for effecting spinal reduction. A part of the saddle thread is thereby left free. The rod is secured in the throat portion and is integral with the throat portion of the saddle member after application of mechanical effort for effecting spinal reduction.

26 Claims, 3 Drawing Sheets

SYSTEM FOR SPINAL OSTEOSYNTHESIS

BACKGROUND OF THE INVENTION

This application is a continuation, of application Ser. No. 08/121,827 filed on Sep. 14, 1993, now abandoned.

The present invention relates to a novel system for spinal osteosynthesis which is simplified and flexible in use and ensures positive results from associated ancillary equipment. The invention also relates to the technique for placement of this osteosynthesis system.

Osteosynthesis of the dorsal, lumbar and sacral spinal portions has been practised for many years. The technique is employed in the case of various therapeutic indications such as traumatology; degeneration, malformation or tumours of the spine; primary or secondary scoliosis; and spinal instability to mention but some.

There are hence numerous pathological cases that require osteosynthesis. One should initially consider deviations of the spine which are particularly common anomalies such as accentuation of dorsal kyphosis, lumbar lordosis, and particularly scoliosis or lateral deviations of the spine. Serious cases of bone or structural scoliosis, accompanied by a rotation of vertebrae about their vertical axis arise for differing reasons. Cases of scoliosis can be congenital, endocrinal, neurological (poliomyelitis) or muscular (myopathy). Sometimes there is no clear etiology and one speaks of idiopathic scoliosis (of the adolescent). We should secondly consider deviations that are due to trauma of the spine, which is frequently the result of an automobile accident. Fracture of the spine without lesion of the medulla (or spinal cord) requires, in serious cases, the spine to be immobilised by osteosynthesis. In the case of a fractured spine with lesions of the medulla, immobilisation by osteosynthesis is useful particularly in cases simply involving compression or contusion of the medulla, in other words where there is the possibility of regression. Finally, it is considered that recourse to osteosynthesis is also effective in the case of malignant tumors. Osteosynthesis is often used in the case of osteoporosis or vertebral epiphysitis which manifests itself at spinal level by the appearance of kyphosis accompanying vertebral deformations (cuneiform and trapezoid vertebrae). Osteosynthesis is often employed in serious cases of arthrosis. It is thus clear that a need exists for spinal osteosynthesis equipment as there are numerous pathological states which require such equipment.

Numerous systems for osteosynthesis have been proposed to date. The Harrington equipment, which is one of the oldest, consists of sub-and supra-laminar hooks and rods. Vertical support is established at the two ends and reduction can only be achieved by distraction. This somewhat outdated equipment suffers from notable disadvantages: limited possibilities of maneuver, poor withstanding ability at its ends and appreciable bulkiness. Cotrel's equipment represented a significant advance, allowing shorter, more stable securing to be achieved and permitting more complex reductions and manipulations. This equipment includes sub-pedicular hooks of a new type, pedicle screws sometimes called "tulip screws", rods having a diamond-finished surface, together with a device for transverse traction or reinforcement of traction. Nevertheless, even though this equipment represents a significant advance over what existed previously, it does still nevertheless suffer from major disadvantages. Thus, apart from the complexity of the Cotrel equipment, reduction manipulations with this equipment are achieved through rods that are molded in advance on anchoring points, whether hook or screw. These manipulations can lead to rupture of the two points of support as a result of excessive force being applied to the bone, or can lead to imperfect reduction occurring, through insufficiency or through excess. Other systems have also been developed and we can mention systems of the screwed plate type, the precursor for which is the Roy-Camille system. This is based on the same principle of reduction at anchoring points starting from plates formed in advance, with the inherent disadvantages of the Cotrel system discussed above. These systems which are now getting somewhat old, sometimes show weak points with breakage of equipment probably related to excess mechanical stresses. The Wiltse system comprises a pedicle screw, a saddle member bridging the screw and receiving initially an aluminum malleable mastering rod which is then reproduced in the form of a rod matching the profile described by the positions of the various screws on the spine, together with a lock nut ensuring the screw and rod are securely fastened together before the surgeon starts to apply mechanical reduction forces. This system suffers from the disadvantages mentioned above in connection with the Cotrel system, as it employs essentially the same principle.

These systems of the prior art do thus present numerous problems. Some systems need to be placed along the sagittal plane which obviously creates a problem of bulkiness combined with the difficulties encountered by the surgeon in gaining access to the area to be operated on. But, most of all, conventional equipment suffers from drawbacks due to the methods employed to date for putting them in place. This is currently the sequence employed in the operating theater: fixing of the screws followed optionally by rigid securing of transverse plates between them, rigid fixing of the rod (which may be pre-formed thanks to the use of a malleable alloy for making a model enabling the position of the screws to be reproduced as a function of the pathology) on the screws, followed by mechanical action using ancillary equipment. This sequence suffers from three major drawbacks. First of all, the rod as initially inserted gets deformed, and the final shape that it should possess cannot always be achieved, with the result that vertebrae remain in a state of hypo- or hyper-reduction. Mechanical stresses are then fairly high and it is sometimes necessary to change the rod during the operation and to replace it by one having an intermediate shape. This can be critical in certain delicate operational situations such as those involving iliac support. The second problem that the prior art systems for osteosynthesis suffer from consist in the fact that the mechanical action that the surgeon exercises is the sum of mechanical action on the bone system and action on the actual osteosynthesis system itself. Thus, the surgeon is not always in a suitable position to evaluate the stresses he is exercising on the vertebrae; in elderly subjects, brittleness of the vertebrae can sometimes lead to the anchoring points being torn out which results in an anchorage having to be achieved on the next vertebra, the effect of which is to increase the length of the osteosynthesis system and as a result the nuisance caused to the patient. Finally, spinal reduction is based on a combination of mechanical action having two degrees of freedom. The practitioner needs in some cases to practise rotation/de-rotation manipulations and in other cases compression-distraction manipulations, or even in certain cases to generate axial pulling forces. There is no current system that enable these independent mechanical actions to be carried out in a satisfactory manner.

SUMMARY OF THE INVENTION

There is hence a requirement for a spinal osteosynthesis system which enables the surgeon to work in the frontal plane, allowing mechanical action to be applied separately to the equipment and to the bones, and guaranteeing a high degree of reliability leading immediately to the form of rod required, and finally enabling rotation/de-rotation, compression/distraction manipulations and generation of axial pulling forces to be readily carried out. This aim, together with other aims is achieved by means of the present invention.

Thus, the present invention provides a system for spinal osteosynthesis comprising:

— a pedicle screw having two threaded portions, the first of which, constituting a pedicle thread, is adapted to be introduced into the pedicle of a vertebra and the second threaded portion constituting a saddle thread is adapted to receive a saddle member;

— a rod;

— at least one saddle member consisting of at least one head provided with a hole of a diameter substantially corresponding to the diameter of the saddle thread provided on said pedicle screw and at least one throat portion the axis of said throat portion being substantially perpendicular to the axis of said head;

— said throat portion including a split passage the size of the opening of which corresponds at least to the diameter of said rod;

— means for securing said saddle member on said screw and adapted to render said pedicle screw at the head thereof integral with said saddle member prior to application of mechanical effort for effecting spinal reduction;

— said securing means and said saddle thread being such that when said securing means is engaged in its locked position, a part of said saddle thread is left free; and — means for securing said rod in said throat portion and for rendering said rod integral with said throat portion of said saddle member after application of mechanical effort for effecting spinal reduction.

The novel spinal osteosynthesis system, according to the invention enables the surgeon to operate on the spine in a more simple, effective and reliable manner. The present spinal osteosynthesis system effectively enables the following operational sequence to be carried out:

a) placement of the pedicle screws;

b) fixing of the saddle member, comprising a head and a throat portion, onto the pedicle screw by placing the entrance to a hole of a diameter substantially equal to the diameter of the saddle thread of the pedicle screw onto the pedicle screw, and locking it onto the saddle thread by means of a fine pitch nut the said nut, once in its locked position, leaving a portion of the saddle thread free;

c) applying mechanical action to the pedicle screws using ancillary equipment consisting of a reduction tube and clamps for distraction, contraction and (de-)rotation; the design of such clamps is generally such that their distal end jaw has a generally crescent moon shape which fits the abovesaid tube; once the desired position is achieved, it is locked by means of clamps;

d) and then, after mechanical action is completed, taking an imprint of the screws and saddles, and producing a corresponding rod;

e) fitting this preformed rod over all the screws, the rod being fitted into the split passage of the throat portion, a means for securing the rod in the throat then being employed to ensure locking of the complete assembly constituting the spine osteosynthesis system in its definitive position;

f) withdrawing the ancillary equipment and terminating the surgical intervention.

This operational sequence, which has been made possible thanks to the novel spinal osteosynthesis system according to the present invention thus allows mechanical action to be applied exclusively to the bones. As the surgeon is now able to only take account of the stresses on the bone system, he is able to avoid applying excessive mechanical forces which could lead, in certain pathological cases such as those of elderly patients for example and when the equipment of the prior art is employed, to breakage of the equipment and more frequently of bone, as well as the tearing out at anchoring points making it necessary to fit the equipment onto the next vertebra. Moreover, the preformed rod is the replica of the rod in its final position whereas, according to the prior art, one would perform the mechanical action on the complete equipment, in other words including the rod. The situation could then arise that having completed the reduction mechanical action, the rod turns out to be unsuitable through being too long or too short or through being subject to excessively high mechanical stresses. Such a situation would either involve leaving the patient with an excessive or insufficient degree of reduction, or recommencing starting from an intermediate position, prolonging the duration of the operation and the time under anaesthetic. Finally, the equipment according to the invention is perfectly suitable for surgical invention in the frontal plane which allows greater freedom of movement; nevertheless, it is of course possible to fit the new spine osteosynthesis system according to the present invention in the sagittal plane.

Now, the disadvantages of the prior art reside in the fact that the sequence of operations employed compared to the above sequence according to the invention, was, for a system of the Cotrel, Wiltse etc. type, as follows: (a), (b), (d), (e), (c), (f), in other words:

a) placement of the pedicle screws;

b) fixing of the saddle member, comprising a head and a throat portion, onto the pedicle screw by placing the entrance to a hole of a diameter substantially equal to the diameter of the saddle thread of the pedicle screw onto the pedicle screw, and locking it onto the saddle thread by means of a fine pitch nut, the said nut, once in its locked position, leaving a portion of the saddle thread free;

d) taking an imprint of the screws and saddles, and producing a corresponding preformed rod the shape of which is adapted to the pathology;

e) fitting this preformed rod over all the screws, the rod being fitted into the split passage of the throat portion, a means for fastening the rod in the throat then being employed to ensure locking of the complete assembly constituting the spine osteosynthesis system, the latter then constituting a statically overdetermined mechanical system;

c) applying mechanical action to the mechanical system, via the pedicle screws, using ancillary equipment consisting of a reduction tube and clamps for distraction, contraction and de-rotation; the design of such clamps is generally such that their distal end jaw has a generally crescent moon shape which fits the abovesaid tube;

f) withdrawing the ancillary equipment and terminating the surgical intervention.

The present system of spine osteosynthesis makes it possible to use the sequence according to the invention.

Numerous variations in the present spinal osteosynthesis system readily accessible to those skilled in the art can be provided, allowing adaptation to each particular pathological case.

The threaded portions of said pedicle screw comprising the saddle thread and the pedicle thread have, respectively fine and coarse pitches.

The pedicle screw includes suitable tightening means to enable it to be screwed into the vertebra. Preferably, the tightening means is comprised of an outer portion of a hexagonal shape on said screw. Advantageously, at least one of the flats of said hexagonal shape mates with a corresponding flat on the head of the saddle member.

The split passage can have any possible form which enables the rod to be introduced into the throat portion and rigidly fixed therein.

In one embodiment, the split passage a has a U-shape whereas in another embodiment, the passage has the shape of the Greek letter omega (Ω).

Any appropriate means for securing the saddle member onto the pedicle screw is suitable, nevertheless a nut is preferred.

Any suitable system for securing the rod in the throat portion of the saddle member is suitable, depending on the respective shape of the throat portion and the rod. It is for example possible to employ a screw with an increasing diameter which is introduced in the space left between the rod and the split passage. When the screw is being tightened, the latter, because of its increasing diameter, exercises a mechanical stress which enables the rod and the throat portion of the saddle member to be locked together; this type of fastening is moreover already employed, notably in ligamentoplasty operations to replace the anterior cruciate ligament of the knee. Any other system is suitable, notably systems employing rings fitted over the rod, or the use of keys providing a wedging effect .

In one embodiment, advantageously when the split passage has an Ω (omega)-shape, the means for securing the rod in the throat portion is a key in the form of a wedging member the inside diameter of which is substantially equal to the diameter of the rod and the outside diameter of which is such that mechanical stress is applied to the saddle member upon rotation or translation of the key.

In another embodiment, when the split passage has a U shape, the means for securing the rod in the throat portion comprises a screw engaging a threaded portion provided in the passage of the throat portion substantially perpendicular thereto and substantially parallel to the pedicle screw. The screw is preferably a grub screw.

The pedicle screw may moreover include other mechanical elements having defined functions. Thus the screw advantageously includes means for limiting its travel so that only the necessary length of the screw is introduced into the pedicle of the vertebra and no lesion or compression of the medular region can occur. Advantageously, the screw includes an external crown between the two threads so that the pedicle screw can come into abutment with the relevant part of the spine.

In one embodiment of the invention, the pedicle screw has a diminishing cross-section in the pedicle thread portion thereof. Advantageously, the bottom portion of the thread profile of the pedicle thread is flat, as described for example, in U.S. Pat. No. 4,653,481, the relevant parts of the description of which relating to the pedicle screw being incorporated herein by reference.

Any nut is suitable for securing the saddle member onto the pedicle screw; nevertheless, a nut provided with grooves designed to receive and guide the tightening means is preferred.

It is desirable also to avoid the saddle member rotating on the screw while the nut is being tightened in order to lock the saddle member onto the screw. Any suitable mechanical system can be employed, such as for example a spline cut into the saddle member thread which corresponds to a projection located on the periphery of the hole in the head of the saddle member. In a preferred embodiment, the head of the saddle member includes a flat and the outer crown of the pedicle screw includes a flat between the two threaded portions, the two flats having corresponding shapes and engaging with each other in order to prevent any possibility of the saddle member rotating on the screw.

In one preferred embodiment, the outer crown situated between the two threaded portions of the pedicle screw is a toothed crown which engages with a corresponding toothed crown on the saddle member in order to prevent any possibility of the saddle member rotating on the screw.

The osteosynthesis system according to the present invention can be fitted onto the spine on one side only, or on both sides. In this latter case, the system according to the present invention includes a suitable mechanical element adapted to link, if required, the two screws fitted on the same vertebra. Preferably, this linking element is a transverse plate which extends between two perpendicular screws on the same vertebra, the plate being rigidly fixed thereon with their two corresponding saddle members and the two corresponding nuts, prior to the mechanical reduction action being applied. The holes at the end of the transverse plates are advantageously of an oval shape, so that only one single plate can be employed for different bone shapes on differing vertebra. The plate can be fitted after reduction, to provide what is known as a "frame mounting".

The saddle member includes at least one throat portion, and there is no reason why the saddle member should not be provided with more than one throat portion. In one preferred embodiment of the present invention, the saddle member includes two throats portions. This dual-throat saddle can be for example employed instead of the traditionally employed "dominos" used for linking separate rods.

Moreover, the pedicle screw is not limited to carrying a single saddle member. According to one embodiment of the invention, the spinal osteosynthesis system comprises two saddle members: an upper and a lower one. The presence of these two saddle members enables two reinforcement axes to be generated and, for example, allows the transverse plate to be replaced by a rod similar to the one employed longitudinally down the spine.

In this embodiment, the two saddle members are locked together still with the aid of a single nut, and the same requirements for absence of rotation between pedicle screw and saddle member apply to the avoidance of rotation between the two saddle members. Thus, in one embodiment of the invention, the lower saddle member includes at least one flat on its head and the upper saddle member includes a lower flat, said upper flat on the lower saddle member and lower flat on the upper saddle member engaging with each other.

In another embodiment, the lower saddle member includes at least one toothed crown on its head and the upper saddle member includes a lower toothed crown, the upper toothed crown on the lower saddle member and lower toothed crown on the upper saddle member engaging with each other.

The new spinal osteosynthesis system is hence perfectly suitable for use when implementing the new surgical operating sequence. The present invention consequently also relates to the use of the spinal osteosynthesis system for spinal reduction, with mechanical reduction being applied prior to the rods being fixed onto the pedicle screws.

BRIEF DESCRIPTION OF THE DRAWINGS

The present invention will now be described in more detail with reference to the attached drawings in which:

FIG. 1b is an elevational view of the screw in FIG. 1a;

FIG. 2b is a cross-sectional view of the pedicle nut taken along line IIb—IIb of FIG. 2a;

FIG. 3b is a top view of the saddle member shown in FIG. 3a;

FIG. 3c is a cross-sectional view taken along the line IIIc—IIIc of FIG. 3a;

FIG. 6b shows the saddle member head which fits onto the crown shown in FIG. 6a;

DETAILED DESCRIPTION OF PREFERRED EMBODIMENTS

Figure 1A:
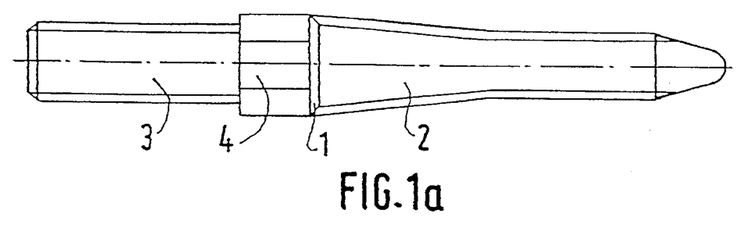
FIG. 1a shows a pedicle screw according to the present invention.

FIG. 1a shows a pedicle screw 1 according to the present invention. This screw 1 includes, apart from means for locking it in the saddle member, two threaded portions, the first of which referred to herein as the pedicle thread 2. The pedicle thread 2 is designed to be introduced into the bony part of the vertebra at the level of the pedicle. The second threaded portion 3 referred to herein as the saddle thread is situated in the portion of the screw that is away from the bone. This thread is designed to firstly receive the saddle member and a lock nut and, optionally the transverse plate, and secondly the ancillary equipment comprising the tubes and clamps defined above. Preferably, the intra-bone (or intra-osseous) portion, in other words that portion that carries the pedicle thread, has a generally conical shape at its upper part and a generally cylindrical shape at its lower part as illustrated in FIG. 1. Nevertheless, a cylindrical shape over its whole length or any other shape is appropriate. Screw 1 may include a crown (which is not shown), the purpose of which is to ensure that the screw comes into abutment on the bone. The screw includes a tightening means whereby a purchase may be obtained on it. This can comprise a slot at the top of the saddle thread, creating a space suitable for insertion of a flat, crosshead or hexagonal screwdriver. Preferably, the tightening means 4 has the general shape of a hexagonal nut enabling it to receive a tightening key. Any other suitable means enabling the screw to be tightened can be employed, for example a hexagonal cavity suitable for receiving a hexagonal key the end of which fits into the hexagonal cavity.

Figure 1B:
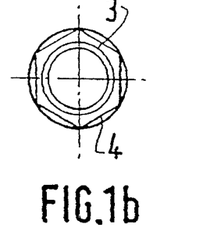

FIG. 1b is an elevational view of the screw 1 according to the invention. Here, the profile of the tightening means 4 together with the thread 3 for the saddle member can be clearly distinguished.

Figure 2A:
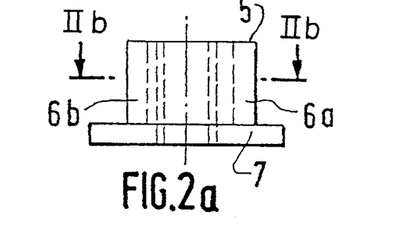
FIG. 2a is a front view of the pedicle nut.

FIG. 2a is a side view of the pedicle nut or saddle-locking nut. The inside diameter and pitch of nut 5 correspond to the diameter and pitch of the saddle thread 3. This nut 5, in accordance with the embodiment shown, includes two lateral grooves 6a and 6b which are designed to receive the tightening instrument. It also includes a crown 7 located in the region of contact.

Figure 2B:
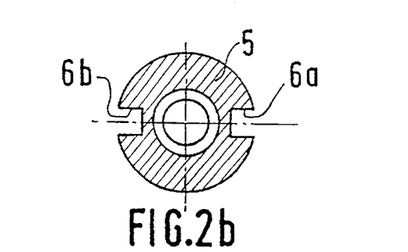

FIG. 2b is a cross-sectional view taken along line IIb—IIb of FIG. 2a of the pedicle nut.

Figure 3A:
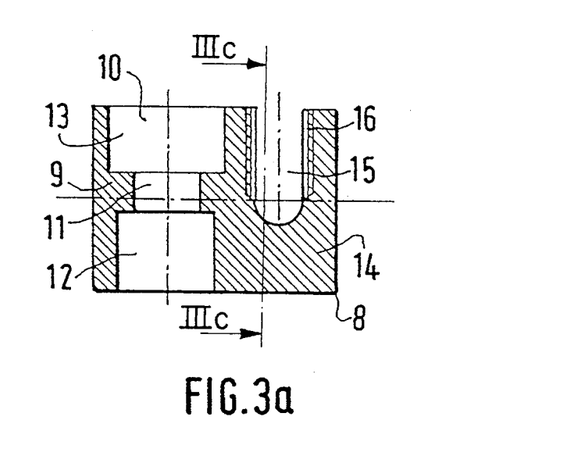
FIG. 3a is a side view of a saddle member according to a first embodiment of the present invention.

FIG. 3a is a side view of the saddle member according to one embodiment of the present invention. This saddle member 8 includes a head 9 carrying a hole 10. The central part 11 of the hole has a diameter similar to the diameter of the saddle thread 3 designed to receive the saddle member. The lower end 12 of the hole, in other words the portion which is closest to the bone, has a sufficient diameter and depth to allow it to fit over and mate with the tightening means 4, represented by a hexagonal profile. The upper portion 13 of the hole, in other words the portion that is furthest from the bone, has a diameter and a depth that are sufficient to accommodate the pedicle nut 5. The saddle member further includes a throat portion 14 which is disposed substantially perpendicular to its head. This throat portion 14 includes a split passage 15 of a diameter that substantially corresponds to the diameter of the rod that fits into the passage. According to the embodiment shown here, the passage has a U-shape. This passage further includes a threaded portion 16 arranged perpendicularly to the passage and substantially parallel to the axis of hole 10, and is designed to receive a locking grub screw (which hereinafter bears the reference 17).

Figure 3B:
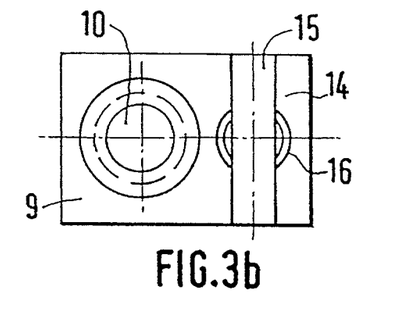

FIG. 3b is a top view of a saddle member 8, in which the following elements can be seen: head 9, hole 10, throat portion 14, passage 15 and thread 16.

Figure 3C:
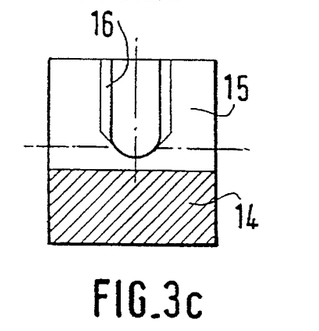

FIG. 3c is a sectional view along the line IIIc—IIIc of FIG. 3a. The section has been taken through the throat portion 14 at the level of passage 15, and shows the thread 16 in greater detail. The latter extends over the whole depth of the passage, although this is not critical for carrying out the invention, which is achieved when the thread extends over a sufficient length for the end of the locking grub screw 17 to come into contact with the rod.

Figure 4:
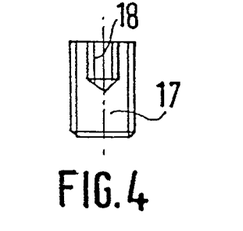
FIG. 4 shows the grub screw for locking the rod in the passage.

FIG. 4 is a view of the locking grub screw 17, which engages with thread 16 provided in passage 15. This grub screw 17 includes a hexagonal-shaped recess 18 adapted to receive an appropriate tool for tightening the grub screw.

Figure 5:
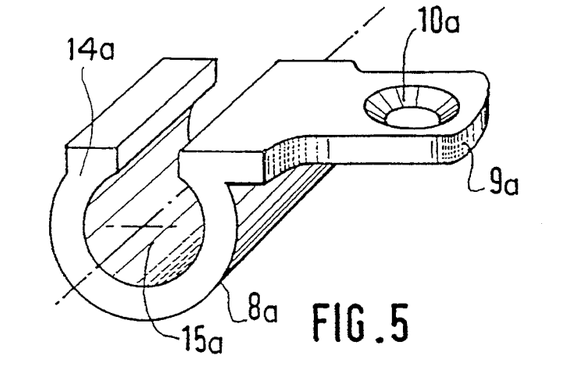
FIG. 5 is a perspective view of the saddle member according to another embodiment of the invention.

FIG. 5 is a perspective view of saddle member 8a according to a further embodiment of the invention. The saddle member 8a comprises a head 9a, carrying a hole 10a the diameter of which corresponds to the saddle thread. The saddle member further includes, arranged substantially perpendicular to its head, a throat portion 14a. This throat portion includes a split passage 15a, its opening corresponding to the diameter of the rod. In the embodiment shown, the split passage has an Ω (omega)-shape which, in FIG. 5, is shown inverted.

Figure 6A:
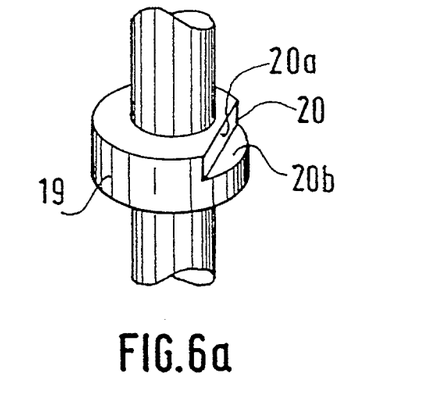
FIG. 6a shows a crown on the pedicle screw.

FIG. 6a is an enlarged view of a crown 19, when the latter is present, for the screw 1. This crown 19 includes a flat 20 consisting of a face 20a which is parallel to the axis of the screw, together with a face 20b which is transverse or perpendicular to the axis of the screw. This flat is designed to fit into the head of the saddle member in order to prevent the saddle member rotating about the screw. Actually, the crown is optional when the tightening means 4 has a hexagonal profile, as in the latter case the tightening means provide the flat face equivalent to face 20a of the crown.

Figure 6B:
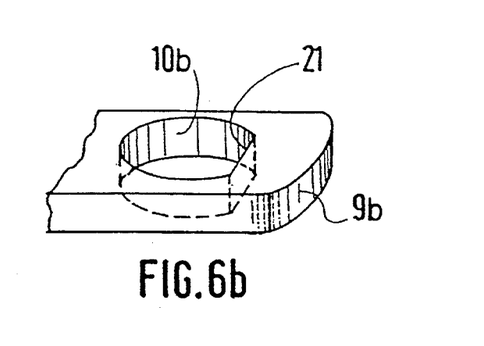

FIG. 6b is a view on an enlarged scale of the head of the saddle member which fits the crown described in FIG. 6a. Head 9b includes, in the lower portion of hole 106, a flat 21 the flat portion of which corresponds to the face 20a on the flat 20 on screw 1 or corresponds to one of the flats on the tightening means 4, when the latter is as shown in FIG. 1a.

Figure 7:
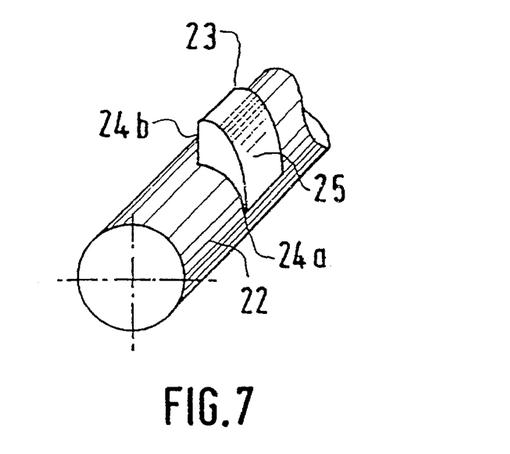
FIG. 7 is a perspective view of a securing means in accordance with one embodiment of the invention.

FIG. 7 is a perspective view of a fastening means in accordance with one embodiment of the invention. This fastening means is placed onto the rod 22 and is referred to as the wedge key below. The inside diameter of this wedge key 23 is substantially the same as the diameter of the rod, covering the latter over substantially a quarter of its periphery. An overlap greater than one half, leading to a slight squeezing effect on the wedge key where for example, the wedge key is symmetrical, can nevertheless be considered advantageous in certain cases. The wedge key 23 is able to turn about the rod 22, with the aid of equipment designed to exercise a rotational force bearing against faces 24a and 24b (the latter being hidden in the figure). The wedge key is eccentric and includes one face 25 having a convex profile extending from face 24a and face 24b (not shown on the figure). This wedge key is chosen to have suitable dimensions and causes, upon its being turned in passage 15 or 15a of the saddle member, a spreading of the latter and the establishment of forces which lock the rod, wedge key and saddle member in a definitive position. The ability of the wedge key to rotate in the passage is ensured by the convex face 25 of the wedge key which only encounters low opposing frictional forces during rotation. The acute angle formed by the faces 25 and 24b ensures the wedge key will not turn once in its final position.

Figure 8:
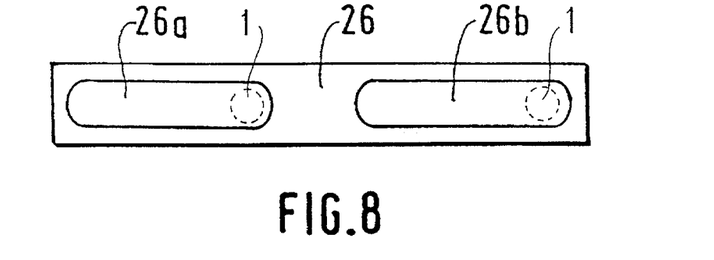
FIG. 8 is a view of the transverse plate according to the invention.

FIG. 8 shows a transverse plate 26 according to the present invention. This plate 26 carries two holes respectively 26a and 26b, of a generally oval shape at each one of its ends. The general shape of this plate and the choice of material allow it to be adapted to the anatomy of the vertebra.

Figure 9:
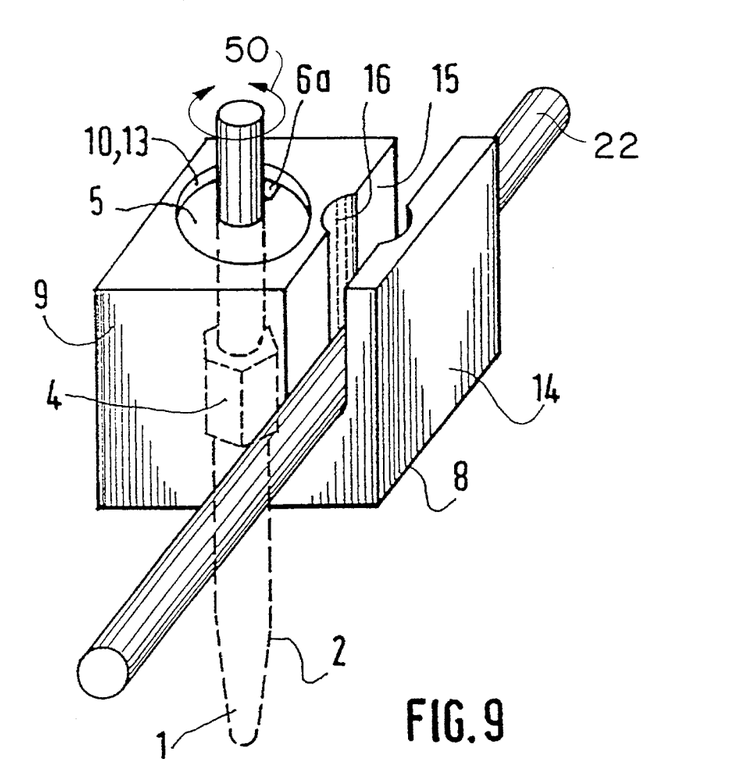
FIG. 9 is a perspective view of the osteosynthesis system according to the present invention.

FIG. 9 is a perspective view of the osteosynthesis system according to the present invention as mounted on a vertebra and at the stage where the grub screw should be fitted in place in order to lock the system together. The dashed lines show that portion of the pedicle screw 1 which is hidden by the saddle member or is in the vertebral bone.

The dimensions of the screw are quite conventional for a classical spine osteosynthesis systems. Thus, regarding the screw, the intra-bone pedicle thread has a length of about 35 to 45 mm, its diameter varying from about 3.5 to about 5.5 mm for the cylindrical portion which is most inward of the bone and from around 4.5 to about 6.5 mm for the conical portion close to the surface of the bone, when the pedicle screw is of a shape similar to that shown in FIG. 1. The saddle thread which is external of the bone has a length of about 20 mm and occasionally more, in order to benefit from an enhanced axial pulling effect, its diameter varying between about 3.5 and about 5.5 mm. The hexagonal tightening means 4 represents about 5 mm of the saddle thread length. Regarding the saddle member, its overall dimensions are typically: height about 10 mm, width about 10 mm and length about 15 mm. When the split passage has a U-shape, the inside diameter of the passage is about 3 mm, in other words the diameter of the rod. The same applies when the split passage has an omega-shape. The hole through the head which fits onto the saddle thread is located about 5 mm from the edge of the saddle member while the split passage is situated at about 3.5 mm from the edge of the saddle and is formed through about half the thickness of the saddle member. The thread provided in the passage has a diameter of about 4 mm and extends from the surface of the saddle member until it reaches the passage. The thickness of the grub screw is thus about 4 mm. The diameter of the rod is about 3 mm and its length is comprised between 100 and 400 mm. The lock nut is about 4 mm thick, the lateral grooves therein having a depth of about 1 mm. The transverse plate has standard dimensions; by way of example, its length can be comprised between about 65 and about 76 mm, its width is about 8 mm and the largest dimension of the oval holes therein is comprised between about 25 and about 30 mm, the smallest dimension being about 4 mm, the hole being situated about 3 mm from the edge of the transverse plate.

This present system for spinal osteosynthesis is fitted into place with the help of ancillary equipment comprising: distraction and compression clamps, a rod carrier, reduction tubes and a suitable screwdriving means. A mechanical action indicated by arrow 50 is applied to the screw 1.

Figure 10:
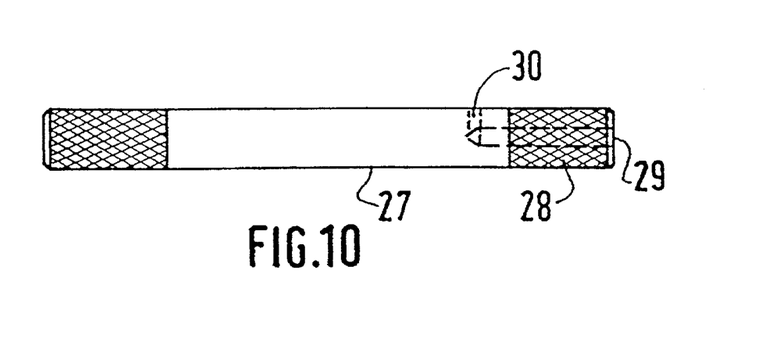
FIG. 10 shows a reduction tube used for carrying out the invention.

FIG. 10 illustrates one characteristic element of the equipment comprising reduction tube 27. This tube includes a distal end 28 which fits onto the free end of the pedicle screw's saddle thread, optionally on the nut. This end includes an internal thread 29 adapted to mate with the saddle thread. A lateral cleaning hole 30 is further provided. Apart from its specific function, this tube enables reduction clamps to operate, the jaws of the latter containing a concave portion which fits onto the reduction tube. These reduction clamps are of two types, one type providing compression when tightened and the other type providing distraction. The compression clamps can also be fitted onto two screws of the same vertebra and be employed for de-rotation. When keys having a wedging effect are used to lock the rod into the split passage, a special key-carrying clamp includes a distal end with arms the end of which includes hooks adapted to apply force to the locking key. It is moreover possible to use any conventional ancillary equipment.

The present osteosynthesis system can be made from any suitable biocompatible material conventionally employed in the prothesis, orthesis, osteosynthesis and like fields. By way of example of a material having the required mechanical and biocompatibility characteristics, titanium alloys can be typically cited as examples. Preferably, the material constituting the present osteosynthesis system is a titanium-based alloy and is advantageously the alloy known as TA6V.

The present invention relating to a novel system for spinal osteosynthesis will now be described in the following examples provided by way of illustration of the implementation of the invention but which in no manner should be considered as limiting the scope thereof.

EXAMPLE 1

Spondylolisthesis

Special elongated screws for exercising an axial pulling force and which include a longer saddle thread are fitted in place on the vertebra needing correction. Initially, the surgeon performs distraction on the overlying and underlying vertebra. It is now possible to perform traction along the axis of the vertebra concerned either by tightening the nut onto the saddle member after the rod has been fitted, or by using a reduction tube having a thread matching the saddle thread of the pedicle screw, the complete assembly being subsequently rendered integral.

EXAMPLE 2

Treatment of degenerative lumbar scoliosis

Pedicle screws are placed on strategic vertebra such as L5, the corresponding saddle members are fitted together with the optional transverse plates, the assembly being locked at each stage by means of a nut.

Reduction tubes are fitted onto each screw and clamps are then used. The surgeon exercises proximal action on the distraction clamps setting up an inter-vertebral space. Following this, he or she operates the compression clamps in the transverse position making it possible to achieve manual de-rotation. Finally, he or she operates the compression clamps on the distal portion of the tubes, thus establishing suitable lordosis. The clamps are then locked thus maintaining the reduction. Suitable fixation rods can now be modelled and fitted into the U-shaped (or respectively, omega-shaped) throat portions of the saddle members. At each stage, the grub screws (or, respectively, wedging keys) are fitted in place and locked. Prior to definitive clamping, and in view of the fact that the inside diameter of the throat portion of the saddle members can be larger than the diameter of the rod, the possibility exists of applying supplementary de-rotation, in order to finely adjust positioning. This is a further advantage of the present invention. The technique is simplified in the case of fractures, where de-rotation is generally not useful, and where distraction and establishment of lordosis are sufficient.

What is claimed is:

1. A system for spinal osteosynthesis comprising:

a pedicle screw having a pedicle thread insertable into the pedicle of a vertebra and a saddle thread;

a rod having a predetermined diameter and a longitudinal axis;

at least one saddle member having at least one head provided with a hole of a diameter substantially corresponding to a diameter of the saddle thread provided on said pedicle screw and at least one throat portion, an axis of said throat portion being substantially perpendicular to the axis of said head;

said throat portion including a split passage having an opening corresponding at least to the diameter of said rod, the rod being insertable into the opening of the split passage in a direction generally perpendicular to the longitudinal axis of the rod;

means for securing said saddle member on said screw to thereby render said pedicle screw at the head thereof integral with said saddle member prior to application of mechanical effort for effecting spinal reduction;

when said securing means is engaged in a locked position, a part of said saddle thread being free; and means for securing said rod in said throat portion to thereby render said rod integral with said throat portion of said saddle member after application of mechanical effort for effecting spinal reduction, said means for securing said rod in said throat portion comprising a screw engaging a threaded portion provided in the passage of said throat portion substantially perpendicular thereto and substantially parallel to said pedicle screw.

2. The system for spinal osteosynthesis according to claim 1, wherein said screw for securing said rod in said throat portion is a grub screw.

3. The system for spinal osteosynthesis according to claim 1, wherein said split passage is generally U-shaped in cross-section.

4. The system for spinal osteosynthesis according to claim 1, wherein the cross section of said split passage is generally omega-shaped.

5. The system for spinal osteosynthesis according to claim 1, wherein said means for securing said saddle member on said pedicle screw is a nut.

6. The system for spinal osteosynthesis according to claim 5, wherein said nut includes grooves for guiding a tightening tool.

7. The system for spinal osteosynthesis according to claim 1, further comprising tightening means between the pedicle thread and the saddle thread for screwing the pedicle screw into vertebra.

8. The system for spinal osteosynthesis according to claim 7, wherein said tightening means comprise an outer hexagonal portion on said pedicle screw.

9. The system for spinal osteosynthesis according to claim 8, wherein the head of said saddle member includes at least one flat engageable with at least one flat of said outer hexagonal portion of said pedicle screw.

10. The system for spinal osteosynthesis according to claim 1, wherein said pedicle screw has a diminishing cross-section in the pedicle thread portion thereof.

11. The system for spinal osteosynthesis according to claim 1, wherein a bottom portion of said pedicle thread is flat.

12. The system for spinal osteosynthesis according to claim 1, wherein said pedicle screw includes an external crown between the said pedicle and saddle threaded portions thereof whereby the pedicle screw abuts with the spine.

13. The system for spinal osteosynthesis according to claim 12, wherein the head of said saddle member includes a flat and the crown of said pedicle screw includes a flat between the two threaded portions, the two flats having corresponding shapes and engaging with each other in order to prevent rotation of said saddle member on said screw.

14. The system for spinal osteosynthesis according to claim 1, further comprising a transverse plate extending between two pedicle screws.

15. A system for spinal osteosynthesis comprising:

a pedicle screw having a pedicle thread insertable into the pedicle of a vertebra and a saddle thread;

a rod having a predetermined diameter and a longitudinal axis;

at least one saddle member having at least one head provided with a hole of a diameter substantially corresponding to a diameter of the saddle thread provided on said pedicle screw and at least one throat portion, an axis of said throat portion being substantially perpendicular to the axis of said head;

said throat portion including a split passage having an opening corresponding at least to the diameter of said rods the rod being insertable into the opening of the split passage in a direction generally perpendicular to the longitudinal axis of the rod;

means for securing said saddle member on said screw to thereby render said pedicle screw at the head thereof integral with said saddle member prior to application of mechanical effort for effecting spinal reduction;

when said securing means is engaged in a locked position, a part of said saddle thread being free; and means for securing said rod in said throat portion to thereby render said rod integral with said throat portion of said saddle member after application of mechanical effort for effecting spinal reduction;

wherein the cross-section of said split passage is generally omega-shaped; and wherein said means for securing said rod in said throat portion is a key formed as a wedging member, an inside diameter of the key being substantially equal to the diameter of the rod and an outside diameter of the key being such that mechanical stress is applied to said saddle member upon one of rotation and translation of said key.

16. The system for spinal osteosynthesis according to claim 15, wherein said means for securing said saddle member on said screw is a nut.

17. The system for spinal osteosynthesis according to claim 16, wherein said nut includes grooves for guiding a tightening tool.

18. The system for spinal osteosynthesis according to claim 15, further comprising tightening means between the pedicle thread and the saddle thread for screwing the pedicle screw into vertebra.

19. The system for spinal osteosynthesis according to claim 18, wherein said tightening means comprise an outer hexagonal portion on said screw.

20. The system for spinal osteosynthesis according to claim 19, wherein the head of said saddle member includes at least one flat engageable with at least one flat of said outer hexagonal portion of said pedicle screw.

21. The system for spinal osteosynthesis according to claim 15, wherein said pedicle screw has a diminishing cross-section in the pedicle thread portion thereof.

22. The system for spinal osteosynthesis according to claim 15, wherein a bottom portion of said pedicle thread is flat.

23. The system for spinal osteosynthesis according to claim 15, wherein said pedicle screw includes an external crown between the said pedicle and saddle threaded portions thereof whereby the screw abuts with the spine.

24. The system for spinal osteosynthesis according to claim 23, wherein the head of said saddle member includes a flat and the outer crown of said pedicle screw includes a flat between the two threaded portions, the two flats having corresponding shapes and engaging with each other in order to prevent rotation of said saddle member on said screw.

25. The system for spinal osteosynthesis according to claim 15, further comprising a transverse plate extending between two pedicle screws.

26. A method for placing a system for spinal osteosynthesis comprising:

a plurality of pedicle screws having a pedicle thread insertable into the pedicle of a vertebra and a saddle thread;

at least a rod having a predetermined diameter and a longitudinal axis;

a plurality of saddle members having at least one head provided with a hole of a diameter substantially corresponding to a diameter of the saddle thread provided on said pedicle screw and at least one throat portion, an axis of said throat portion being substantially perpendicular to the axis of said head;

said throat portion including a split passage having an opening corresponding at least to the diameter of said rod, the rod being insertable into the opening of the split passage in a direction generally perpendicular to the longitudinal axis of the rod;

means for securing at least one of said plurality of saddle members on said screws to thereby render said pedicle screw at the head thereof integral with said saddle member prior to application of mechanical effort for effecting spinal reduction;

when said securing means is engaged in a locked position, a part of said saddle thread being free; and means for securing said rod in said throat portion to thereby render said rod integral with said throat portion of said saddle member after application of mechanical effort for effecting spinal reduction;

the method comprising the steps of:
  a) providing the plurality of pedicle screws, the rod and the plurality of saddle members;
  b) placing the pedicle screws;
  c) fixing said saddle members onto said pedicle screws by placing an entrance of the hole of said saddle member onto the pedicle screw, and locking it thereon by said nut, once in its locked position, leaving a portion of said saddle thread free;
  d) applying mechanical action to the pedicle screws through at least a reduction tube;
  e) after mechanical action is completed, producing at least a corresponding rod; and
  f) fitting said corresponding rod over all the screws, the rod being fitted into the split passage of said throat portion, and securing the rod in the throat portion to ensure locking of the complete assembly constituting the spine osteosynthesis system in position.

* * * * *